United States Patent
Mastrangelo

(10) Patent No.: US 9,981,902 B2
(45) Date of Patent: May 29, 2018

(54) PROCESS FOR PRODUCTION OF AN ESTER AND DIOL FROM RECLAIMED CARPET MATERIAL

(71) Applicant: Columbia Insurance Company, Omaha, NE (US)

(72) Inventor: John Charles Mastrangelo, Ringgold, GA (US)

(73) Assignee: Columbia Insurance Company, Ohama, NE (US)

( * ) Notice: Subject to any disclaimer, the term of this patent is extended or adjusted under 35 U.S.C. 154(b) by 0 days. days.

(21) Appl. No.: 15/332,362

(22) Filed: Oct. 24, 2016

(65) Prior Publication Data

US 2017/0113995 A1 Apr. 27, 2017

Related U.S. Application Data

(60) Provisional application No. 62/245,452, filed on Oct. 23, 2015.

(51) Int. Cl.
C07C 67/00 (2006.01)
C07C 67/03 (2006.01)

(52) U.S. Cl.
CPC .................................. C07C 67/03 (2013.01)

(58) Field of Classification Search
CPC ..................................................... C07C 67/03
See application file for complete search history.

(56) References Cited

U.S. PATENT DOCUMENTS

| | | |
|---|---|---|
| 2,628,207 A | 2/1953 | Smith, Jr. et al. |
| 2,884,443 A | 4/1959 | Siggel et al. |
| 3,488,298 A | 1/1970 | Barkey et al. |
| 3,501,420 A | 3/1970 | Stevenson |
| 3,818,071 A | 6/1974 | Chilton |
| 3,907,868 A | 9/1975 | Currie et al. |
| 4,028,159 A | 6/1977 | Norris |
| 4,216,337 A | 8/1980 | Baba et al. |
| 4,304,925 A | 12/1981 | Watanabe et al. |
| 4,929,749 A | 5/1990 | Gupta et al. |
| 5,101,064 A * | 3/1992 | Dupont .................. C07C 67/03 560/78 |
| 5,230,530 A | 7/1993 | Iriyama et al. |
| 5,252,615 A * | 10/1993 | Rao .......................... C08J 11/22 521/48 |
| 5,298,530 A | 3/1994 | Gamble et al. |
| 5,319,128 A | 6/1994 | Dupont et al. |
| 5,395,858 A | 3/1995 | Schwartz, Jr. |
| 5,481,024 A | 1/1996 | Hertenstein et al. |
| 5,504,122 A | 4/1996 | Michel et al. |
| 5,518,188 A | 5/1996 | Sharer |
| 5,535,945 A | 7/1996 | Sferrazza et al. |
| 5,672,729 A | 9/1997 | Naujokas |
| 5,710,315 A * | 1/1998 | Gallagher ............... C07B 61/00 560/78 |
| 5,898,063 A | 4/1999 | Stefandl |
| 5,898,934 A | 5/1999 | Hunter et al. |
| 5,948,934 A | 9/1999 | Cruz-Gomez et al. |
| 5,952,520 A | 9/1999 | Naujokas |
| 6,029,916 A | 2/2000 | White |
| 6,191,177 B1 | 2/2001 | Ekart et al. |
| 6,292,277 B1 | 9/2001 | Kikinis |
| 6,472,557 B1 | 10/2002 | Pell, Jr. et al. |
| 6,867,322 B1 | 3/2005 | Kato et al. |
| 7,276,621 B2 | 10/2007 | Cook et al. |
| 7,357,971 B2 * | 4/2008 | Bieser ...................... B32B 7/12 428/95 |
| 7,635,099 B1 | 12/2009 | Meredith et al. |
| 7,784,719 B1 | 8/2010 | Wingard |
| 7,799,942 B2 | 9/2010 | Osborne et al. |
| 7,893,122 B2 | 2/2011 | Fregoso-Infante et al. |
| 8,017,662 B2 | 9/2011 | Hoover, Jr. et al. |
| 8,360,348 B2 | 1/2013 | Levy et al. |
| 8,455,387 B2 | 6/2013 | Lindall et al. |
| 8,864,057 B2 | 10/2014 | Bork et al. |
| 2008/0242751 A1 | 10/2008 | Kurian et al. |
| 2013/0109763 A1 | 5/2013 | Daute et al. |
| 2013/0112727 A1 * | 5/2013 | Bork ...................... B29B 17/02 225/2 |
| 2013/0296525 A1 | 11/2013 | Waibel et al. |
| 2014/0288325 A1 | 9/2014 | Yang et al. |

FOREIGN PATENT DOCUMENTS

| | | |
|---|---|---|
| WO | WO-2007/044017 A1 | 4/2007 |
| WO | WO-2013/143824 A1 | 10/2013 |

OTHER PUBLICATIONS

Akovali, G. et al. Solvolysis, Frontiers in the Science and Technology of Polymer Recycling NATO ASI series. 1998; 351:425-36 (Abstract Only).

Datye et al., Poly(ethylene terephthalate) waste and its utilisation: A review, Resources and Conservation. 1984; 11(2):117-41 (Abstract Only).

Dupont, L.A. et al., Degradative transesterification of terephthalate polyesters to obtain DOTP plasticizer for flexible PVC. J Vinyl Technol. 1993; 15(2):100-4 (Abstract Only).

Dutt et al., A Review on Synthesis of value added products from polyethylene terephthalate (PET) waste. Poly Sci Series B. 2013; 55(7-8):430-52.

Helms et al., Reverse Logistics for Recycling: Challenges Facing the Carpet Industry, Greening the Supply Chain, pp. 117-135 (Abstract Only).

Liu, F. et al., Alcoholysis of poly(ethylene terephthalate) to produce dioctyl terephthalate with sub-and super-critical isooctyl alcohol. J Anal Appl Pyrolysis. 2013; 99: 16-22.

Paszun et al., Chemical Recycling of Poly(ethylene terephthalate). Ind Eng Chem Res. 1997; 36:1373.

(Continued)

Primary Examiner — Jafar Parsa
Assistant Examiner — Blaine G Doletski
(74) Attorney, Agent, or Firm — Ballard Spahr LLP

(57) ABSTRACT

The current invention pertains to a process for producing a terephthalate ester comprising: providing reclaimed carpet material comprising a polyester component; and reacting the polyester component with an alcohol having from 6 to 20 carbon atoms and under conditions effective to produce a terephthalate ester; wherein 15-40% of the mass of the terephthalate ester is derived from the polyester present in the reclaimed carpet material.

47 Claims, 2 Drawing Sheets

(56) References Cited

OTHER PUBLICATIONS

Realff et al., Carpet recycling: Determining the reverse production system design. J Polymer-Plastics Technol Plastics Technol Eng. 1999; 38(3):547-67 (Abstract only).
Shukla, S.R. et al., Recycling of waste PET into useful textile auxiliaries. Waste Manag. 2008; 28(1):51-6 (Abstract Only).
Wang, Fiber and Textile Waste Utilization. Waste Biomass Valor. 2010; 1:135-43.

* cited by examiner

PROCESS FOR PRODUCTION OF AN ESTER AND DIOL FROM RECLAIMED CARPET MATERIAL

CROSS-REFERENCE TO RELATED APPLICATIONS

This Application claims the benefit of priority to U.S. Provisional Application No. 62/245,452, filed on Oct. 23, 2015, which is incorporated herein by reference in its entirety.

FIELD OF THE INVENTION

The present invention pertains to production of an ester, such as a terephthalate ester, and diol from a reclaimed carpet material. More particularly, the present invention pertains to a process utilizing a reclaimed carpet material that comprises a polyester component to form a terephthalate ester and a diol. The present invention further pertains to formation of a terephthalate ester having, for example and without limitation, about 15-40% of the mass of the terephthalate ester derived from the polyester component present in the reclaimed carpet material. The present invention further relates to a process of recycling a reclaimed carpet material. The present invention further pertains to a process of making a diol wherein substantially all of the diol is derived from the polyester component present in the reclaimed carpet material.

BACKGROUND OF THE INVENTION

Terephthalate polyester resins are thermoplastic polymers that are widely used in the plastics industry. Terephthalate polyesters resins are used in the manufacturing of films, bottles, plastic containers of all kinds, carpets and carpet products, fibers, fabrics, all kinds of textile materials, strapping, and the like.

A major problem with reprocessing terephthalate polyester resins is that when heated in the presence of moisture, polyesters may partially hydrolyze to polymer of severely reduced molecular weight. Polyesters must therefore be very dry during processing, typically containing less than 50 ppm moisture, in order to prevent unacceptable levels of hydrolysis. In view of this challenge, conventional reprocessing of the polyesters represents a technological and economic challenge.

Furthermore, with the growing use of terephthalate polyester products, major waste disposal problems and expenses have been encountered by both the manufacturers and the consumers. For example, the carpet industry is one of the industries that are facing a growing challenge of disposing of polyester based products. Unlike two common types of nylon (6,6 and 6), which can be recycled back into a new carpet or reused in other applications, polyester based carpet currently has no economically viable afterlife. Whereas nylon (6,6 and 6), for example, can technically chemically processed and then re-extruded into useful articles. The same cannot be said for the polyester which loses its tensile strength after its initial use as a carpet. The large quantities of the sold polyester based carpets creates availability of more than 100 MM lbs/yr of post-consumer carpet with no more economical outlet than use as a boiler fuel.

One of the possible ways for recycling polyester face fiber reclaimed carpet products can be producing other phthalate esters, and particularly terephthalate esters. Terephthalate esters are mainly used as plasticizers added to plastic to increase its flexibility, transparency, durability, and longevity. Terephthalate esters can be used to soften various polymers for example polyvinyl chloride (PVC). Due to the safety concerns, previously popular lower molecular weight phthalates are being replaced by high-molecular-weight terephthalates, or those with more than 6 carbons in their backbone, which gives them, increased permanency and durability, and decreased toxicity. Additionally, terephthalate esters are fortuitously less biologically active (i.e. estrogen mimicking) than phthalate esters. A common manufacturing process for terephthalate esters is based on the transesterification reaction. Unfortunately, the conventional process is slow, making the process economically undesirable.

Accordingly, there is a need for an efficient process for producing a terephthalate ester. Still further, there is a need for a recycling process for reclaimed carpet materials comprising polyester components. It would be further desirable to have a process for producing a terephthalate ester from a reclaimed carpet material. And even further, it would be desirable to have a process for producing a diol from a reclaimed carpet material. These needs and other needs are at least partially satisfied by the present invention.

SUMMARY OF THE INVENTION

In accordance with the purpose(s) of the invention, as embodied and broadly described herein, the invention, in one aspect, relates to a process for producing a terephthalate ester. The process generally comprises the steps of providing reclaimed carpet material comprising a polyester component and reacting the polyester component with an alcohol having from 6 to 20 carbon atoms. The reaction is performed under conditions effective to produce a terephthalate ester. According to aspects of the invention, the process can provide a terephthalate ester wherein, for example and without limitation, about 15-40% of the mass of the terephthalate ester is comprised of component material that is derived from the polyester initially present in the reclaimed carpet material.

Also disclosed herein is a process for recycling a reclaimed carpet material. This process generally comprises the steps of reacting a reclaimed carpet material comprising a polyester component with an alcohol having from 6 to 20 carbon atoms in the presence of a catalyst at a temperature from about 160° C. to about 260° C. to form a reaction mixture. The reaction mixture comprises a terephthalate ester having about 15-40% of the mass derived from the reclaimed carpet material; a diol, wherein substantially all of the diol is derived from the polyester component present in the reclaimed carpet material; and unreacted residual materials and products.

Further disclosed herein is a process for producing a diol. This process generally comprises the steps of providing reclaimed carpet material comprising a polyester component; and reacting the polyester component with an alcohol having from 6 to 20 carbon atoms and under conditions effective to produce a diol. According to some aspects, substantially all of the produced diol is derived from the polyester component present in the reclaimed carpet material.

Additional aspects of the invention will be set forth, in part, in the detailed description, and claims which follow, and in part will be derived from the detailed description, or can be learned by practice of the invention. It is to be understood that both the foregoing general description and the following detailed description are exemplary and explanatory only and are not restrictive of the invention as disclosed.

DETAILED DESCRIPTION OF THE INVENTION

Figure 1:
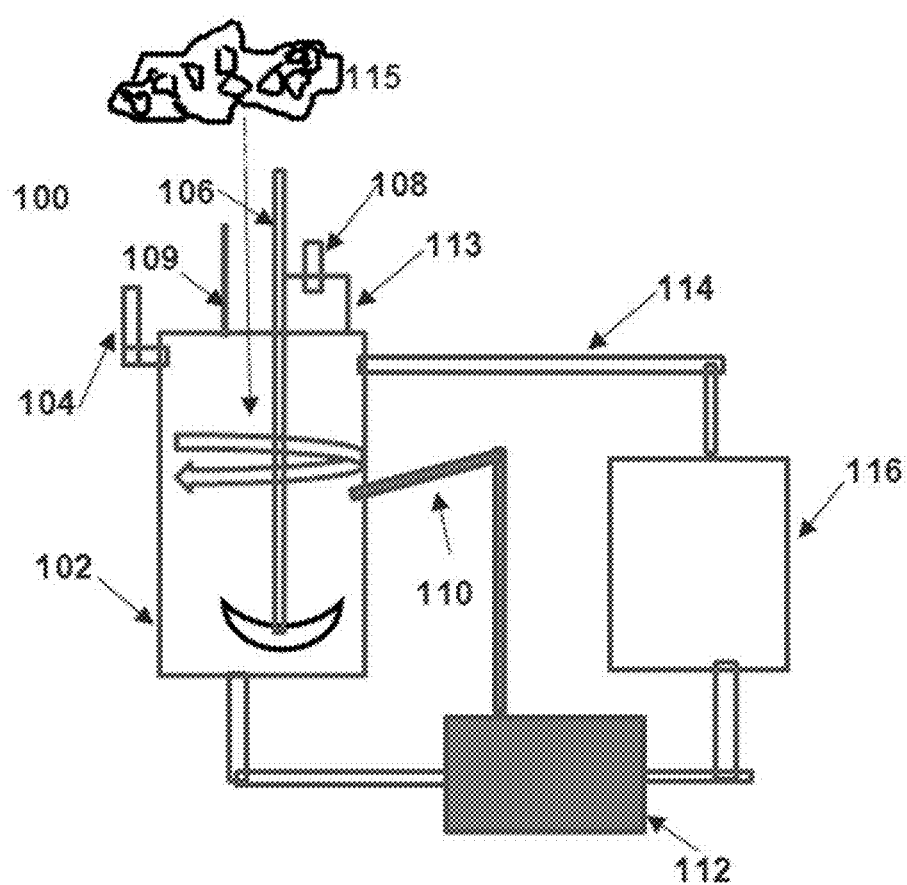
FIG. 1 shows an exemplary apparatus for producing a terephthalate ester and a diol.

The present invention can be understood more readily by reference to the following detailed description, examples, drawings, and claims, and their previous and following description. However, before the present compositions, articles, devices, systems, and/or methods are disclosed and described, it is to be understood that this invention is not limited to the specific compositions, articles, devices, systems, and/or methods disclosed unless otherwise specified, as such can, of course, vary. It is also to be understood that the terminology used herein is for the purpose of describing particular aspects only and is not intended to be limiting.

The following description of the invention is also provided as an enabling teaching of the invention in its best, currently known aspect. To this end, those of ordinary skill in the relevant art will recognize and appreciate that changes and modifications can be made to the various aspects of the invention described herein, while still obtaining the beneficial results of the present invention. It will also be apparent that some of the desired benefits of the present invention can be obtained by selecting some of the features of the present invention without utilizing other features. Accordingly, those of ordinary skill in the relevant art will recognize that many modifications and adaptations to the present invention are possible and can even be desirable in certain circumstances and are thus also a part of the present invention. Thus, the following description is provided as illustrative of the principles of the present invention and not in limitation thereof.

Various combinations of elements of this disclosure are encompassed by this invention, e.g. combinations of elements from dependent claims that depend upon the same independent claim.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

All publications mentioned herein are incorporated herein by reference to disclose and describe the methods and/or materials in connection with which the publications are cited.

It is also to be understood that the terminology used herein is for the purpose of describing particular aspects only and is not intended to be limiting. As used in the specification and in the claims, the term "comprising" may include the aspects "consisting of" and "consisting essentially of"

Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used herein, the singular forms "a," "an" and "the" include plural referents unless the context clearly dictates otherwise. Thus, for example, reference to an "alcohol" includes aspects having two or more alcohols unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" mean that the subsequently described event or circumstance may or may not occur, and that the description includes instances where said event or circumstance occurs and instances where it does not.

As used herein, the terms "polyester component" or "polyester" refers to a category of polymers that contain the ester functional group in their main chain. Polyesters components disclosed herein include naturally occurring chemicals, such as in the cutin of plant cuticles, as well as synthetics produced through step-growth polymerization. An unlimiting example of polyester components includes any long-chain synthetic polymer composed of at least 85% by weight of an ester of a substituted aromatic dicarboxylic acid, including but not restricted to substituted terephthalic units, p(—R—O—CO—$C_6H_4$—CO—O—)$_x$ and parasubstituted hydroxy-benzoate units, p(—R—O—CO—$C_6H_4$—O—)$_x$. In certain examples, the polyester component comprises polyethylene terephthalate (PET) homopolymer and copolymers, polypropylene terephthalate (PPT) homopolymer and copolymers and polybutylene terephthalate (PBT) homopolymer and copolymers, and the like, including those that contain comonomers such as cyclohexanedimethanol, cyclohexanedicarboxylic acid, and the like. It is further understood that the polyester component can be included in any fiber present in the reclaimed carpet material, for example and without limitation, a face fiber of the reclaimed carpet material. It is further understood that the polyester component can be included in the backing or any other structural parts of the reclaimed carpet material. It is further understood, that the polyester component can be included in the adhesive composition.

The terms "polyamide" or "polyamide component" can be used interchangeably, and as utilized herein, are defined to be any long-chain polymer in which the linking functional groups are amide (—CO—NH—) linkages. The term polyamide is further defined to include copolymers, terpolymers and the like as well as homopolymers and also includes blends of two or more polyamides. An example of polyamide component includes one or more of nylon 6, nylon 66, nylon 10, nylon 612, nylon 12, nylon 11, or any combinations thereof. It is further understood that polyamide component can be included in any fiber present in the reclaimed carpet material, for example, a face fiber. It is further understood that the polyamide component can be included in the backing or any other structural parts of the reclaimed carpet material.

As defined herein, the terms "polyolefin" or "polyolefin components" refer to any class of polymers produced from a simple olefin (also called an alkene with the general formula $C_nH_{2n}$) as a monomer. In some aspects, the polyolefins include, but are not limited to, polyethylene, polypropylene, both homopolymer and copolymers, poly(1-butene), poly(3-methyl-1-butene), poly(4-methyl-1-pentene) and the like, as well as combinations or mixtures of two or more of the foregoing. It is further understood that the polyolefin component can be included in any fiber present in the reclaimed carpet material, for example a face fiber of the reclaimed carpet material. It is further understood that the polyolefin component can be included in the backing or any other structural parts of the reclaimed carpet material. Yet further it is understood that the polyolefin component can be present in the adhesive composition.

As defined herein, the terms "polyurethane" or "polyurethane components" refer to any class of polymers composed of a chain of organic units joined by carbamate (urethane, $R_1$—O—CO—$NR_2$—$R_3$, wherein R1, R2 and R3 are the same or different) links. The polyurethane components can be present in any part of the reclaimed carpet material, for example, carpet backings.

The terms "carpet" or "carpet tile" are used herein in the manner as would be recognized by one of ordinary skill in the art. As used herein, and unless the context clearly indicates otherwise, the term carpet is used to generically include broadloom carpets, carpet tiles, area rugs, and synthetic turf. To that "broadloom carpet" means a broadloom textile flooring product manufactured for and intended to be used in roll form. "Carpet tile" denotes a modular floor covering, conventionally in 18"×18", 24"×24", or 36"×36" squares, but other sizes and shapes are also within the scope of the present invention.

As used herein, the term "reclaimed carpet material" include a new carpet, post-industrial carpet, or post-consumer carpet. The term "reclaimed carpet material" also includes the residue from carpet shearing process, often referred to as "carpet carcass." This comprises backing material with the residual fiber that remains attached after mechanical shearing.

As used herein, the term "reclaimed carpet material" is also intended to include fibrous material comprised of two or more different types of fibers in which one type of fiber has a lower thermal decomposition, or oxidation, or pyrolysis temperature than the other. One example of such a material is trunk liner mat, which is comprised of non-woven polyethylene terephthalate (PET), which can be considered as the face fiber material, and a polyolefin binder, which can be considered as the backing material. Another example is a padding made from recycled carpet which may be comprised of PET or nylon fiber, and/or polypropylene fiber, and one or more backing components and adhesives.

As used herein, the term "post-consumer carpet" refers to a carpet or a carpet product that has been generated by end users of the product which can no longer be used for its intended purpose. The post-consumer carpet includes carpets that have been used in residential, commercial, and industrial applications, and subsequently have been discarded.

As used herein, the term "post-industrial carpet" refers to a carpet or a carpet product that is a byproduct of the carpet or carpet product manufacturing that has been diverted from the manufacturing waste stream.

As used herein, the term "alcohol" refers to any organic compound in which the hydroxyl functional group (—OH) is bound to a carbon atom. As used herein, the term "diol" refers to any organic compound in which the two hydroxyl functional groups (—OH) are bound to carbon atoms. Alcohols described herein include a mixture of two or more alcohols, wherein each alcohol in the mixture can be present in any amount relative to each other. Further, alcohols described herein include straight chain alcohols, branched alcohols, cyclic aliphatic group alcohols, aromatic group alcohols, an alkaryl group, an aralkyl group alcohols, and any combinations thereof.

The term "alkyl group" as used herein is a branched or unbranched saturated hydrocarbon group of 1 to 30 carbon atoms. A "lower alkyl" group is an alkyl group containing from one to six carbon atoms. A "higher alkyl" group is alkyl group containing from six to 30 carbon atoms.

The term "aryl group" as used herein is any carbon-based aromatic group, including, but not limited to, benzene, naphthalene, etc. The term "aromatic" also includes a "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, carboxylic acid, or alkoxy.

The term "aralkyl" as used herein is an aryl group having an alkyl, alkynyl, or alkenyl group as defined above attached to the aromatic group. An example of an aralkyl group is a benzyl group. The term "alkaryl" refers to an alkyl-substituted aryl radical (such as ethyl-phenyl).

As used herein, the term "copolymer" refers to a polymer formed from two or more different repeating units (monomer residues). By way of example and without limitation, a copolymer can be an alternating copolymer, a random copolymer, a block copolymer, or a graft copolymer.

As used herein, the term "substantially all," when used in reference to a composition, refers to at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature or component.

As used herein, the term or phrase "effective," "effective amount," or "conditions effective to" refers to such amount or condition that is capable of performing the function or property for which an effective amount or condition is expressed. As will be pointed out below, the exact amount or particular condition required will vary from one aspect to another, depending on recognized variables such as the materials employed and the processing conditions observed. Thus, it is not always possible to specify an exact "effective amount" or "condition effective to." However, it should be understood that an appropriate effective amount will be readily determined by one of ordinary skill in the art using only routine experimentation.

The term "fiber" as used herein includes fibers of extreme or indefinite length (i.e. filaments) and fibers of short length (i.e., staple fibers).

References in the specification and concluding claims to parts by weight of a particular element or component in a composition or article, denotes the weight relationship between the element or component and any other elements or components in the composition or article for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

A weight percent of a component, or weight %, or wt. %, unless specifically stated to the contrary, is based on the total weight of the formulation or composition in which the component is included.

While aspects of the present invention can be described and claimed in a particular statutory class, such as the system statutory class, this is for convenience only and one of ordinary skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The present invention may be understood more readily by reference to the following detailed description of various aspects of the invention and the examples included therein and to the Figures and their previous and following description.

In some aspects, described herein is a process generally comprising the steps of providing reclaimed carpet material comprising a polyester component and reacting the polyester component with an alcohol having from 6 to 20 carbon atoms. The reaction is performed under conditions effective to produce a terephthalate ester. According to aspects of the invention, the process can provide a terephthalate ester wherein, for example and without limitation, about 15-40% of the mass of the terephthalate ester is comprised of component material that is derived from the polyester initially present in the reclaimed carpet material.

In certain aspects, the provided reclaimed carpet material, comprising a polyester component, and the alcohol, having from 6 to 20 carbon atoms, form a reaction mixture. In some aspects, the alcoholysis, esterification, or transesterification reaction between a polyester component and an alcohol occurs in a reaction mixture. In one aspect, the reaction mixture is exposed to conditions effective to produce a terephthalate ester. In another aspect, the produced terephthalate ester has about 15-40% of the mass derived from the polyester component present in the reclaimed carpet material. In certain aspects, the reaction mixture exposed to conditions effective to produce a terephthalate ester can further comprise unreacted products, residual (unreacted) reagents, and any other products that can be formed under specified conditions.

In certain aspects, the process for producing a terephthalate ester of the present invention pertains to any reclaimed carpet material. In some aspects, the reclaimed carpet material comprises a post-consumer carpet, post-industrial carpet, or a combination thereof. In yet other aspect, the reclaimed carpet material comprises a broadloom carpet, a carpet tile, an area rug, a synthetic turf, or any combinations thereof. In yet further aspects, the reclaimed carpet material is a broadloom carpet, a carpet tile, an area rug, a synthetic turf, or any combinations thereof.

In certain aspects of the disclosure, the reclaimed carpet material can further comprise at least one of a face fiber, a mineral filler, a backing material, an adhesive composition, a contaminant, or any combinations thereof. In some aspects, the reclaimed carpet material is provided as a whole product. In yet another aspect, the provided reclaimed carpet material can be mechanically or thermally treated prior to reacting with the alcohol.

In some aspects, the reclaimed carpet material comprises a face fiber. The face fiber material can comprise, for example, a nylon or a polyester, or a mixture of nylons, or a mixture of polyesters, or a mixture of nylons and polyesters. In yet further aspects, the face fiber can comprise polyolefin fibers. In one aspect, the polyolefins include, but are not limited to, polyethylene, polypropylene, both homopolymer and copolymers, poly(1-butene), poly(3-methyl-1-butene), poly(4-methyl-1-pentene) and the like as well as combinations or mixtures of two or more of the foregoing. In another aspect, the face fiber comprises one or more of nylon 6, nylon 66, nylon 10, nylon 612, nylon 12, nylon 11, or any combinations thereof. In a further aspect, the face fiber comprises nylon 6 or nylon 66. In yet another aspect, the face fiber is nylon 6. In a still further aspect, face fiber is nylon 66. In some aspects, the face fiber is polyester comprising polyethylene terephthalate, polypropylene terephthalate, polybutylene terephthalate, or any combinations thereof. In one aspect, the face fiber is polyethylene terephthalate. In another aspect, the face fiber is polypropylene terephthalate, also known as polytrimethylene terephthalate (PTT). In yet another aspect, the face fiber is polybutylene terephthalate. In some aspects, the reclaimed carpet material can comprise face fiber comprising any combinations of polyesters, nylons, and olefins.

As described, in certain aspects, the reclaimed carpet material can comprise mineral fillers. Exemplary and non-limiting fillers that can be incorporated in the reclaimed carpet material can include calcium carbonate, fly-ash, recycled calcium carbonate, aluminum trihydrate, talc, nano-clay, barium sulfate, barite, barite glass fiber, glass powder, glass cullet, metal powder, alumina, hydrated alumina, clay, magnesium carbonate, calcium sulfate, silica, glass, fumed silica, carbon black, graphite, cement dust, feldspar, nepheline, magnesium oxide, zinc oxide, aluminum silicate, calcium silicate, titanium dioxide, titanates, glass microspheres, chalk, and any combinations thereof. In one aspect, the mineral filler comprises calcium carbonate. In another aspect, calcium carbonate can further comprise impurities. In certain aspects, the impurities present in calcium carbonate can comprise other common minerals in varying amounts, for example, and without limitation magnesium carbonate, barium carbonate, silica, and the like. In a still further aspect, the mineral filler is predominantly calcium carbonate. It is further understood that the mineral fillers disclosed herein can be present in any parts of the reclaimed carpet material. In one exemplary aspect, the mineral fillers are present in the backings. In another exemplary aspect, the mineral fillers are present in the adhesive compositions. In yet another exemplary aspect, the mineral fillers are present in the backings and the adhesive compositions. In certain aspects, the mineral fillers can be present in reinforcing components, such as, for example and without limitation, a carpet scrim.

It is further understood that the mineral fillers can be present in the reclaimed carpet material in any amount necessary to obtain a carpet material with desirable properties. In some aspects, the mineral fillers can be present in the reclaimed carpet material in an amount from about 5 wt. % to about 90 wt. % of the total weight of the reclaimed carpet material, including exemplary values of about 10 wt. %, about 15 wt. %, about 20 wt. %, about 25 wt. %, about 30 wt. %, about 35 wt. %, about 40 wt. %, about 45 wt. %, about 50 wt. %, about 55 wt. %, about 60 wt. %, about 65 wt. %, about 70 wt. %, about 75 wt. %, about 80 wt. %, and about 85 wt. %. Still further, the mineral fillers disclosed herein can be present in any amount within a range derived from the above values. For example, the mineral filler composition can be present in an amount from about 25 wt. % to about 80 wt. % of the total weight of the reclaimed carpet material, 30 wt. % to about 70 wt. % of the total weight of the reclaimed carpet material, or even 40 wt. % to about 65 wt. % of the total weight of the reclaimed carpet material.

According to aspects of the disclosed process, the reclaimed carpet material can further comprise a backing material. The backing material can comprise one or more primary backing, one or more secondary backing, or a combination thereof. In some aspects, the backing material can be a foam. In one aspect, the backing material can comprise a polyolefin, polyurethane, polyester, polyvinyl chloride, or any combinations thereof.

In certain aspects of the disclosure, the provided reclaimed carpet material can further comprise an adhesive composition. In some aspects, various parts of the reclaimed carpet material can be held together with an adhesive composition. As it would be readily understood by one of ordinary skill in the art, since the adhesive composition is used to hold various parts of the reclaimed materials, some of these parts will also comprise the adhesive composition. For example and without limitation, if the secondary backing is attached to the primary backing and the face fiber by employing the adhesive composition, it is understood that both the primary backing, face fiber, and the secondary backing will comprise the adhesive composition. It is further understood that, for example, the face fiber can be substantially encapsulated in the adhesive material. In yet other aspects, the adhesive composition can be employed as a backing in the reclaimed carpet material. In some aspects, the adhesive material can comprise the same polymers as face fibers, a primary backing or a secondary backing. It is also understood that in these cases if heat applied is above a temperature of the melting point of the adhesive composition, the integral fusing can occur. However, as one of ordinary skill in the art would readily appreciate, if the adhesive composition comprises a polymer different from face fibers, primary backing, or a secondary backing, the integral fusing does not occur. It is understood that by the term "same polymer," it is meant that the monomer units of the polymers are of the same chemistry, although their molecular or morphological attributes may differ. Conversely, by the term "different polymer," it is meant that, irrespective of any molecular or morphological differences, the monomer units of the polymers are of different chemistries.

The adhesive composition present in the provided reclaimed carpet material in some aspects of the current invention can be any adhesive composition known in the art. In some exemplary aspects, the adhesive composition can comprise latex adhesive compositions. In other aspects, the adhesive composition can comprise various polyolefin materials such as, for example and without limitation, ethylene vinyl acetate (EVA), polypropylene or polyethylene (e.g., low density polyethylene (LDPE), linear low density polyethylene (LLDPE) or substantially linear ethylene polymer, or mixtures thereof). In yet further aspects, the adhesive composition can comprise an EVA hotmelt, a vinyl acetate ethylene (VAE) emulsion, carboxylated styrene-butadiene (XSB) latex copolymer, a styrene-butadiene resin (SBR) latex, a butadiene methyl methacrylate (BDMMA) latex, an acrylic latex, an acrylic copolymer, a styrene copolymer, butadiene acrylate copolymer, a polyolefin hotmelt, polyurethane, polyolefin dispersions and/or emulsions, and any combinations thereof. In other aspects, the adhesive composition can comprise cross-linked and uncross-linked polymers. In one aspect, the adhesive composition can comprise at least one homogeneously branched ethylene polymer comprising interpolymer of ethylene with at least one $C_3$-$C_{20}$ α-olefin. In another aspect, the adhesive composition can comprise a crosslinked styrene-butadiene copolymer, a crosslinked ethylene vinyl acetate copolymer, or a combination thereof. In further aspects, the adhesive compositions can comprise ethylene acrylic acid (EAA) copolymers, ionomers and maleic anhydride grafted polyethylene compositions. The adhesive composition can be present in any amount conventionally used in the art and defined by the desired properties for a specified use of the carpet material prior to its reclamation.

In certain aspects, the provided reclaimed carpet materials can further comprise flame retardants, surfactants, tackifiers, thickeners, defoaming agents, and/or a dispersion enhancer. It is understood that any known in the art flame retardants, surfactants, tackifiers, thickeners, defoaming agents, and/or a dispersion enhancer can be present in the reclaimed carpet material in any amount defined by the desired properties for a specific use of the carpet material prior to its reclamation.

It is also understood that according to the aspects of this disclosure, the reclaimed carpet materials can further comprise various contaminants. The contaminants can comprise a consumer deposited contaminant, a manufacturing process contaminant, or a combination thereof. Further, in exemplary aspects, the consumer deposited contaminant can comprise food particles, soil particles, hair, bodily fluids, food fluids, staples, tack strips, or any combinations thereof. It is further understood that the reclaimed carpet material utilized in the described process can contain any contaminants originating in the use of the carpet material. In yet other exemplary aspects, the manufacturing process contaminant comprises oil, lubricants, dust, scrap, dyes, pigments, anti-stain, anti-soil, bale strapping, wire, or any combinations thereof.

According to the aspects of the disclosed process, the polyester component present in the provided reclaimed carpet material can comprise any polyester known in the art. In some aspects, the polyester component comprises terephthalate based esters. In certain aspects, the polyester component comprises polyethylene terephthalate (PET) homopolymers and copolymers, polypropylene terephthalate (PPT/PTT) homopolymers and copolymers, polybutylene terephthalate (PBT) homopolymers and copolymers, and the like, including those that contain comonomers such as cyclohexanedimethanol, cyclohexanedicarboxylic acid, and the like. In other aspects, the polyester component comprises polyethylene terephthalate glycol modified (PETG). In yet other aspects, the polyester component comprises a crystalline polyethylene terephthalate (CPET). In still further aspects, the polyester component comprises a polycyclohexylenedimethylene terephthalate (PCT) or glycol modified polycyclohexylenedimethylene terephthalate (PCTG). In still further aspects, the polyester component comprises polyethylene terephthalate, polypropylene terephthalate, polybutylene terephthalate, or any combinations thereof. It is understood that the polyester component utilized in the current invention is not limited to be present in any specific structural part of the reclaimed carpet material. In one exemplary aspect, the polyester component can be present in a face fiber. In another exemplary aspect, the polyester component can be present in a backing material. In a yet further exemplary aspect, the polyester component can be present in an adhesive composition. In additional exemplary aspect, the polyester component can be present in a face fiber, in a backing material and in an adhesive composition.

The alcohol component utilized to provide the reaction mixture can be any alcohol or alcohol mixtures known in the art. In some aspects, alcohols utilized in the processes of the current invention comprise alcohols having from 6 to 20 carbon atoms inclusively. In other aspects, the alcohols can comprise a straight chain, branched or cyclic aliphatic alcohol or using an aromatic, alkaryl or aralkyl alcohol. It is well understood that the choice of the alcohol is dependent upon the desired final product. In some aspects, the alcohol is a straight chain or branched alcohol having from 6 to 20 carbon atoms. In other aspects, a wide variety of alcohols can be used in the context of the present invention. In some aspects, an alcohol utilized in the disclosed process can comprise hexanol, 2-ethyl-1-hexanol, isonanol, isodecanol, isoeicosanol, octanol, decanol, tricadenol, pentadecanol, or any combinations thereof. In yet other aspects, the alcohol comprises 2-ethyl-1-hexanol.

It is further understood that in some aspects of the current disclosure, to achieve a desirable product, the alcohol is present in a stoichiometric excess amount relative to the polyester component present in the reclaimed carpet material. In some exemplary aspects, the alcohol is present in an amount of at least about 10% more, at least about 50% more, at least about 100% more, at least about 150% more, at least about 200% more, at least about 250% more, at least about 300% more, or at least about 500% more of a stoichiometric amount of the polyester component present in the reaction mixture.

According to the aspects of the disclosed process, the conditions effective to produce the terephthalate ester can further comprise a temperature in the range of from about 160° C. to about 260° C., including exemplary values of about 170° C., about 180° C., about 190° C., about 200° C., about 210° C., about 220° C., about 230° C., about 240° C., and about 250° C. Still further, a temperature can be in any range derived from the above values. For example, a temperature can be in the range from about 170° C. to about 200° C., from about 200° C. to about 210° C. or even about 230° C. to about 240° C. It is further understood that any means known in the art can be utilized to achieve a desirable temperature. For example and without limitation, the reactor containing the reaction mixture can be heated utilizing an oil bath or an electrical heating element.

Further, the conditions effective to produce the terephthalate ester in some aspects can comprise manipulating the reaction temperature by changing a reaction pressure. In exemplary aspect, if there is a need in raising a reaction mixture overall temperature, the reaction mixture can be slightly pressurized. In yet other aspects, the reaction can be carried out under vacuum. In some other aspects, conditions effective to produce the terephthalates ester can further comprise a pressure from near 0 psi to about 50 psi, including exemplary values of about 0.0001 psi, about 0.001 psi, about 0.005 psi, about 0.008 psi, about 0.01 psi, about 0.05 psi, about 0.08 psi, about 0.1 psi, about 0.14 psi, about 0.5 psi, about 0.8 psi, about 1 psi, about 5 psi, about 10 psi, about 14 psi, about 20 psi, about 25 psi, about 30 psi, about 35 psi, about 40 psi, and about 45 psi. Still further, a pressure can be in any range derived from the above values. For example, a pressure can be from about 0.0001 psi to about 0.01 psi, about 0.01 psi to about 0.1 psi, or even about 0.01 psi to about 30 psi.

In certain aspects, the disclosed process can include refluxing the reaction mixture. Accordingly to these aspects, the conditions effective to produce the terephthalate ester can further comprise refluxing for a period of about 0.5 hours to about 20 hours, including exemplary values of about 1 hour, about 1.5 hours, about 2 hours, about 2.5 hours, about 3 days, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 10.5 hours, about 11 hours, about 11.5 hours, about 12 hours, about 12.5 hours, about 13 hours, about 13.5 hours, about 14 hours, about 14.5 hours, about 15 hours, about 15.5 hours, about 16 hours, about 16.5 hours, about 17 hours, about 17.5 hours, about 18 hours, about 18.5 hours, about 19 hours, and about 19.5 hours. Still further, a period of time can be in any range derived from the above values. For example, a period of time can be about 0.5 hours to about 6 hours, about 2 hours to about 10 hours, or even about 5 hours to about 12 hours. It is further understood that any means known in the art can be utilized to achieve a desirable temperature and pressure. In some aspects, the reactor containing the reaction mixture can be heated utilizing an oil bath or an electrical heating element. In other aspects, the pressure can be regulated by a pump.

According to aspects of the disclosed process, the conditions effective to produce the terephthalate ester can further comprise the presence of a catalyst. In some aspects, any suitable catalysts commonly utilized for an alcoholysis, esterification, or transesterification reaction can be used. In some exemplary aspects, a titanium based catalyst can be used. For example, a catalyst comprising tetraisopropyl titanate ($Ti(OC_3H_7)_4$) can be utilized in the disclosed method. In yet further exemplary aspects, the catalyst can comprise a tin based catalyst or zinc based catalyst. For example, catalysts such as tin(II) oxalate or zinc acetate can be utilized. In yet further aspects, the catalyst used in the present invention can be present in an ash component. The ash component can be received from any combustion reaction. In some aspects, the ash is obtained by heating any material that contains calcium carbonate at a temperature of about 600° C. or greater, about 700° C. or greater, about 800° C. or greater, about 900° C. or greater, about 1,000° C. or greater, about 1,100° C. or greater, or about 1,200° C. or greater. In certain aspects, the ash component can comprise CaO. In other aspects, the ash comprising high CaO content can be obtained by calcination, or heating to a temperature of at least 800° C. In some aspects, the ash is obtained by calcination, for example, of a reclaimed carpet material. It is further understood that in certain aspects, the ash content can further comprise oxides and sulfides of other metals, for example and without limitation, oxide and sulfides of magnesium, sodium, iron, silicon, or any combinations thereof.

In some aspects, the catalysts used in the aspects of the present disclosure are not acidic in nature. In yet other aspects, the catalysts used in the present invention are neutral or basic in nature. It is further understood that the terms "acidic," "neutral," or "basic" have the meaning that is commonly accepted in the field of chemistry and would be readily recognized by one of ordinary skill in the art.

The process described herein can produce esters having the general formula (I):

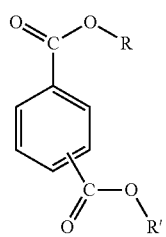

(I)

wherein R and R' are the same or different and comprise a straight chain, branched or cyclic aliphatic group, an aromatic group, an alkaryl group or an aralkyl group, each group having from 6 to 20 carbon atoms. In some aspects, the produced terephthalate esters have the same or different R and R' comprising a straight chain or a branched alkyl group having from 6 to 20 carbon atoms.

In further aspects, at least 90% by weight of the produced ester can be characterized as having the general formula (II):

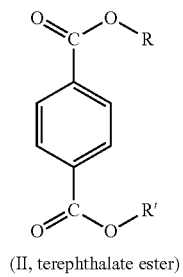

(II, terephthalate ester)

In certain aspects, at least about 91%, at least about 92%, at least about 93%, at least about 94%, at least about 95%, at least about 96%, at least about 97%, at least about 98%, or at least about 99% of produced terephthalate ester is of a general formula (II). In some aspects, the produced terephthalate ester is of a general formula (II), wherein the phenyl ring is substituted in a para-position comprises R and R' that can be same or different and their exact structure will dependent on a type of alcohol used in the reaction.

In yet further aspects, about 10% or less by weight of the produced ester is in a form of or has the chemical structures of:

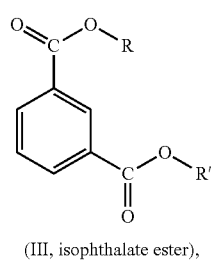

(III, isophthalate ester),

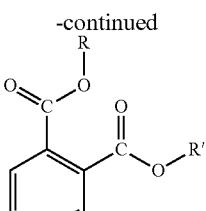

(IV, phthalate ester), or a combination thereof.

In some other aspects, about 9% or less, about 8% or less, about 7% or less, about 6% or less, about 5% or less, about 4% or less, about 3% or less, about 2% or less, or about 1% or less of the produced terephthalate ester is of a general formula (III), (IV), or a combination thereof. It is understood that if a combination of (III), wherein the phenyl ring is substituted in a meta-position, and (IV), wherein the phenyl ring is substituted in a ortho-position, is present, both (III) and (IV) can be in any weight % ratio relatively to each other. It is further understood that R and R' can be the same or different and their exact structure will dependent on a type of alcohol used in the reaction.

It is further understood that terephthalate ester of a general formula (I) can comprise terephthalate esters of a general formula (II), general formula (III), general formula (IV), or any combinations thereof.

As described above, in some aspects, alcohol is a mixture of alcohols. In one exemplary aspect, the mixture of alcohols can comprise two alcohols. In this exemplary aspect, three different compounds of a general formula (I) can be obtained: a compound, wherein both substituents R and R' are derived from the first alcohol; a compound wherein both substituents R and R' are derived from the second alcohol; and a compound wherein substituents R and R' bear different groups derived from the both alcohols. It is understood that the proportions of the alcohols forming the desired alcohol mixture will vary, depending on the targeted composition of the final products.

In certain aspects of the invention, the produced terephthalate ester has about 10-60% of mass derived from the polyester present in the reclaimed carpet material. In exemplary aspects, about 15%, about 20%, about 25%, about 30%, about 35%, about 40%, about 45%, about 50%, and about 55% mass of the produced terephthalate ester is derived from the polyester present in the reclaimed carpet material. In certain aspects, the produced terephthalate ester has 15-40% of mass derived from the polyester present in the reclaimed carpet material.

According to the aspects of the disclosed process, the produced terephthalate ester of a general formula (II) can comprise di-n-hexyl terephthalate, dioctyl terephthalate, diisononyl terephthalate, diisodecyl terephthalate, di-n-octyl n-decyl terephthalate, di-n-tridecyl n-pentadecyl terephthalate, or diisoeicosyl terephthalate. In yet other aspects, the terephthalates ester having a general formula (II) is di-n-hexyl terephthalate. In still further aspects, the terephthalates ester having a general formula (II) is dioctyl terephthalate. In still further aspects, the terephthalates ester having a general formula (II) is diisononyl terephthalate. In still further aspects, the terephthalates ester having a general formula (II) is diisodecyl terephthalate. In still further aspects, the produced terephthalates ester of a general formula (II) is di-n-octyl n-decyl terephthalate. In still further aspects, the produced terephthalates ester of a general formula (II) is di-n-tridecyl n-pentadecyl terephthalate. In still further aspects, the produced terephthalates ester of a general formula (II) is di-n-octyl n-decyl terephthalate diisoeicosyl terephthalate.

It is understood that a molecular weight of the produced terephthalate ester will vary, depending on an alcohol used in the reaction. The desired terephthalate ester can be formed by one of ordinary skill in the art selecting an appropriate alcohol. In some exemplary aspects, the produced terephthalate ester formed from a C6 alcohol has a molecular weight of about 334 g/mol. In yet another exemplary aspect, the produced terephthalate ester formed from a C20 alcohol has a molecular weight of about 754 g/mol.

It is further understood that the reclaimed carpet material utilized in the current disclosure can be used as provided. In other aspects, the reclaimed carpet material can be mechanically or thermally treated prior to the process of forming a terephthalate ester. In some aspects, the reclaimed carpet material is size reduced. In these aspects, the size reduction of the reclaimed carpet material does not result in the substantial change in a reclaimed carpet material composition. It is understood that the size reduction of the reclaimed carpet material can be done by any techniques and methods known in the art, including, but are not limited to cutting, shredding, milling, grinding, shearing, and the like.

According to the aspects of the process described herein, reaction under the conditions effective to produce the terephthalate ester portion of the process can further produce a diol. As one of ordinary skill in the art would readily appreciate, the term "diol," as used herein refers to a chemical compound containing two hydroxyl groups. It is further understood that a specific diol formed under the conditions effective to produce the terephthalate ester will depend on a specific polyester component present in the reclaimed carpet material. In some aspects, the formed diol comprises 1,2-ethanediol also called "ethylene glycol," 1-3-propanediol, or 1,4-butanediol. In yet other aspects, the diol is ethylene glycol. In still further aspects, the diol is 1-3-propanediol. In yet further aspects, the diol is 1,4-butanediol. In certain aspects, substantially all of the diol is derived from the polyester component present in the reclaimed carpet material. In yet other aspects, at least about 80%, at least about 85%, at least about 90%, at least about 95% or about 100% of the formed diol is derived from the polyester component present in the reclaimed carpet material.

In the aspects where the diol is formed, the formed diol is present in the reaction mixture. In certain aspects, the diol is separated from the reaction mixture. In yet other aspects, the diol is separated from the terephthalate ester. In still further aspects, the diol is separated from any residual reactants optionally present in the reaction mixture. In aspects, where the residual reactants are present in the reaction mixture, the residual reactants can comprise an amount of an alcohol present in the reaction mixture in a stoichiometric excess amount relative to a polyester component prior to the reaction. In some aspects, the residual reactant can comprise an amount of an alcohol that did not react with a polyester component. It is understood that the formed diol can be separated from the terephthalate ester and an alcohol that did not react with a polyester component utilizing any known in the art techniques or methods such as an oil-water separator like a Dean-Stark trap. In some exemplary aspects, the diol can be separated by distillation. In other aspect, the diol can be separated from the reaction mixture with use of a condenser. It is further understood, that in some aspects, separating the formed diol from the reaction mixture can farther accelerate the rate of reaction between the polyester component and the alcohol.

According to the aspects of the current disclosure, the reaction mixture can further comprise unreacted products, wherein the unreacted products can be formed as a precipitate. In some aspects, the unreacted products are a slurry comprising parts of the reclaimed carpet material that were not dissolved or reacted under conditions effective to produce a terephthalate ester. In certain aspects, the unreacted products are separated from the produced terephthalate ester. In other aspects, the unreacted products are separated from the residual reagents. In yet further aspects, the unreacted products are separated from the formed diol by any means known in the art. In some aspects, the separation is performed by distillation. In other aspects, the separation is performed by filtration or centrifugation. It is understood that any filtration methods known in the art can be utilized. In some aspects the filtration is performed at higher than atmospheric pressure, or at atmospheric pressure, while in other aspects, the filtration is performed under vacuum.

In some aspects, the unreacted products separated from the formed terephthalate ester and from residual reagents can be further utilized in various processing steps. For example, in some aspects, the unreacted products can be combusted at a temperature of at least about 600° C., at least about 700° C., at least about 800° C., at least about 900° C., at least about 1,000° C., at least about 1,100° C., or at least about 1,200° C. In yet other aspects, the combustion is conducted for at least about 0.5 hour, at least about 1 hour, at least about 1.5 hours, at least about 2 hours, at least about 2.5 hours, at least about 3 hours, at least about 3.5 hours, at least about 4 hours, at least about 4.5 hours, or at least about 5 hours. The combusted unreacted products can form ash that can be further utilized in the process described herein as a catalyst. In other aspects, the unreacted process can be further utilized in anaerobic degradation (i.e. pyrolysis) to small molecule hydrocarbon (i.e. liquid fuel) substances. In yet other aspects, the unreacted products can be utilized as a fuel. As one of ordinary skill in the art would readily appreciate, the aspects where these combusted unreacted products are reused in the inventive process allow conducting the disclosed process in the "cradle to cradle" mode. As used herein, the term "cradle to cradle mode" refers to a process of forming a product that is essentially waste free.

Figure 2:
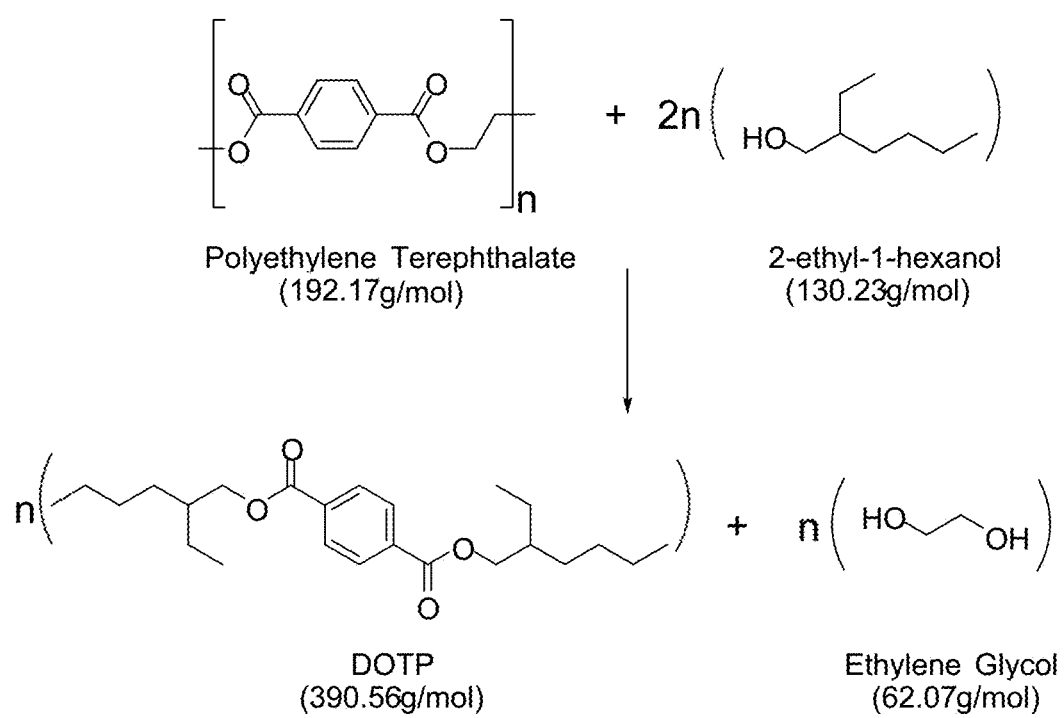
FIG. 2 shows an exemplary balanced reaction scheme.

FIG. 1 schematically shows an exemplary aspect of this invention. Specifically, FIG. 1 demonstrates a schematic of exemplary process sequence 100. In some aspects, the reclaimed carpet material 115 comprising a polyester component is charged into a reactor 102. An alcohol and a catalyst are added to the reactor to form a reaction mixture. The reactor 102 is equipped with a vacuum line 104, agitator 106, a distillation column 109, a vapor return line 110, an oil water separator (trap) 113, and a liquid return line 114. The trap is connected to a reflux condenser 108. Thus, the trap 113 is supplied with condensate from the reflux condenser 108. When trap 113 overflows oil is returned to reactor 102. The reaction mixture is stirred with an agitator 106 at vacuum or pressure of 0-10 psig, and an overhead temperature of 180-200° C. The trap 113 is filled with a sufficient amount of water disposed at the bottom of the trap. The trap 113 also collects diol formed during the reaction in the bottom water layer. Vapors of the unreacted (residual) alcohol used in the reaction are returned back to the reactor 102 though trap 113. After sufficient time required achieving equilibrium, the hot reaction slurry is pumped out of reactor through filter 112 to the holding tank 116 to obtain a filter cake and a filtrate. The filter is further heated and vacuum can be applied to recover substantially all residual liquids from the filter cake via vapor return line 110. The filtrate liquid is returned to the reactor from the holding tank by means of the liquid return line 114. The residual alcohol is distilled out of reactor 102 using distillation line 109, first at atmospheric pressure, then under about 50 Pa (about 0.007 psi) vacuum until distillation ceases (the maximum overheads temperature reaches about 60° C.). The distilled residual (unreacted) alcohol is retained for reuse in the next batch of reaction. Vacuum distillation at much higher temperature (170-190° C. overheads) and lower vacuum (about 20 Pa, or about 0.003 psi) is required to collect a crude terephthalate ester product. The steps of adding the alcohol and the catalyst can be repeated to achieve higher conversion rate to the desired terephthalate product. The formed dry filter cake is removed from the filter 112 and can be further combusted to form a catalyst to be utilized in the subsequent steps. The formed diol is recovered from the trap. It is further understood that the diol removal can occur at any step of the process of forming terephthalate ester. An exemplary reaction scheme is demonstrated in FIG. 2. As one of ordinary skill in the art would readily appreciate, the subscript "n" associated with polyethylene terephthalate is used to indicate a number of repeating polyethylene terephthalate units in the polymer. In some aspects, the subscript "n" denotes the degree of polymerization. It is further understood that the subscript "n" is an integral number, wherein its final value is defined by the final number of the repeating units in the polymer. In aspects wherein the subscript "n" is 1, the polyethylene terephthalate unit is defined as a monomer. In some other aspects, the subscript "n" is from 1 to 250, in yet other aspects, the subscript "n" is from 1 to 1,000. It is understood that the highest limit of the subscript "n" is not limited and can depend on the molecular weight of the polymer and its degree of polymerization. It is further understood that in order to stoichiometrically form "n" molecules of DOTP and "n" molecules of ethylene glycol from the "n" units of PET, "2n" molecules of 2-ethyl-1-hexanol are required.

Alternatively, the reaction mixture can be refluxed until equilibrium is achieved and then the formed liquids are filtered, distilled and purified. Additional alcohol can be added to the residual reaction solids and reflux can be further continued until reaching a new equilibrium. The process can be repeated. A number of repetitions can be easily determined by one of ordinary skill in the art, to achieve a maximum yield. In some aspects, the reaction yield is about 55% to about 100%, including exemplary values of about 60%, about 65%, about 70%, about 75%, about 80%, about 85%, about 90%, about 95%, about 97%, about 98%, and about 99%. In yet other aspects, the yield is about 95% to about 100%, including exemplary values of about 95.5%, about 96%, about 96.5%, about 97%, about 97.5%, about 98%, about 98.5%, about 99%, about 99.5%, about 99.6%, about 99.7%, about 99.8%, and about 99.9%. Still further, a reaction yield for forming terephthalate ester can be in any range derived from the above values. For example, a reaction yield can be about 60% to about 85%, about 85% to about 97%, or even about 95.5% to about 99.9%.

In yet other aspects of this invention, the described process can be utilized as a recycling process of a reclaimed carpet material. The recycling process generally comprises the steps of reacting a reclaimed carpet material comprising a polyester component with an alcohol having from 6 to 20 carbon atoms in the presence of a catalyst at a temperature from about 160° C. to about 260° C. to form a reaction mixture. The reaction mixture comprises a terephthalate ester having about 15-40% of the mass derived from the reclaimed carpet material; a diol, wherein substantially all of the diol is derived from the polyester component present in the reclaimed carpet material; and unreacted residual materials and products. It is understood that in some aspects, the process of recycling a reclaimed carpet material described herein represents a cradle to cradle process allowing use of waste products to form new and useful products.

Further disclosed herein is a process for producing a diol. This process generally comprises the steps of providing reclaimed carpet material comprising a polyester component; and reacting the polyester component with an alcohol having from 6 to 20 carbon atoms and under conditions effective to produce a diol. According to some aspects, substantially all of the produced diol is derived from the polyester component present in the reclaimed carpet material.

It is further understood that any reclaimed material described herein can be used to form desirable diol products. For example and without limitation, the reclaimed carpet material is a broadloom carpet, a carpet tile, an area rug, a synthetic turf, or any combinations thereof. It is further understood that any polyester component described herein can be utilized. The polyester component can be present in any part of the reclaimed carpet material as described. In exemplary aspects, the polyester component comprises polyethylene terephthalate, polypropylene terephthalate, polybutylene terephthalate, or any combinations thereof. In yet other aspect, the choice of the polyester component is dependent upon the desired diol to be formed. It is further understood that any alcohols described herein can be used in the process. For example and without limitation, the alcohol can comprise hexanol, 2-ethyl-1-hexanol, isonanol, isodecanol, isoeicosanol, octanol, decanol, tricadenol, pentadecanol, or any combinations thereof. In some aspects, the formed diol is ethylene glycol. In yet other aspects, the formed diol is 1,3-propanediol. In yet further aspect, the formed diol is 1,4-butanediol.

The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Example 1

A 40 gram of a size-reduced post-consumer carpet material comprising a polyethylene terephthalate (PET) component was introduced into a 500 ml three neck flask with a stir bar. About 120 ml of 2-ethyl-1-hexanol was added to the flask followed by addition of a catalyst comprising a 0.4 g tetraisopropyl titanate, $Ti(OC_3H_7)_4$. A 5 ml Dean Stark trap was fitted to one neck of the flask and was filled with an additional amount of 2-ethyl-1-hexanol. 2 ml of water has been also added to the trap. The added water and 2-ethyl-1-hexanol forms a two-phase solution, with water on the bottom of the trap. A needle for flushing the reaction system with argon gas was put through a septum placed on the second neck, and the third neck of the flask was stoppered. The flask was immersed in an oil bath up to the level of the necks. The oil was heated to cause the contents of the flask to boil. An increase in the volume of the liquid layer at the bottom of the trap was interpreted as evidence of ethylene glycol being produced in the flask, boiling out as a vapor mixture with 2-ethyl-1-hexanol, and preferentially partitioning into the aqueous phase present in the trap. After 15-20 hours of reflux (oil temperature 200-210° C.) the carpet had lost all cohesion, the fiber was gone and a dark colored slurry with undissolved solids had formed.

When the rate of increase in volume of the bottom layer in the Dean Stark trap slowed down, the condenser atop the trap was temporarily removed and a needle was used to withdraw the contents of the trap. The bottom layer was crudely separated (and saved) from the top layer and the top layer was injected back into the trap. About 2 ml of fresh water was then introduced back into the trap and reflux was continued. After about 24 hours of reflux over 4 days the reaction completed and the formed di-octyl-terephthalate (DOTP) was isolated and purified.

Upon completion of the reaction the cooled slurry was mixed with petroleum ether and followed by vacuum filtration. The filter cake was dried and saved as a grey crumbly solid. The filtrate was evaporated first at atmospheric pressure, then at moderate vacuum to remove the petroleum ether. Vacuum of 30-45 Pascal was applied and approximately 50 ml of clear liquid was distilled/collected at an overheads temperature not exceeding 55° C. Higher vacuum of 17-19 Pascal was applied and a formed yellow oil was distilled off with a maximum overheads temperature of 185° C. Upon completion of the distillation about 23 g of oil was collected, leaving a dry, hard, maroon colored residue in the distillation pot.

A portion of the formed yellow oil was purified using column chromatography. About 8.4 g of yellow oil was loaded onto a one inch diameter, 6 inch deep silica column. The chromatography was carried out with gradient elution starting with petroleum ether and ending with about 1% ethyl acetate in petroleum ether. For a complete elution total volume of eluent of about 300 ml was required. Upon completion of elution about 8.0 grams of clear, colorless oil was collected, indicating more than 95% of recovery yield of colorless oil.

A second portion of the formed yellow oil, in an amount of about 2 g, was treated with activated charcoal (coconut, 8-12 mesh) to determine if a colorless liquid could be obtained by a solvent-free method (i.e. instead of the column chromatography described immediately above). The oil was soaked in a bottle containing charcoal pellets in a volume ratio of 2 to 1 (oil to charcoal pellets). The mixture of oil and charcoal pellets remained undisturbed overnight and then filtered through a 0.2 micron retention polytetrafluoroethylene (PTFE) and glass microfiber membrane (to remove a small amount of light fluffy precipitate which formed). Upon the filtration completion, a colorless oil was obtained. The quality of the oil obtained by column purification was compared to the oil obtained by purification with use the charcoal pellets using ultraviolet (UV) spectroscopy. The UV measurement of the oil absorption was measured at wavelengths of 290-360 nm in about 1 wt % in cyclohexane. It was demonstrated that the oil obtained by purification with use of charcoal pellets is higher than the oil purified by column chromatography.

The purified oil was analyzed using gas chromatography combined with mass spectrometry (GC/MS). It was found that the clear oil contains at least about 95.5% of the desired, DOTP, product. It was also found that about 3% of the mass can be related to one of DOTP isomers, for example, an isomer substituted at the meta positions rather than at the para position as in DOTP. It was concluded that at least about 98.5% of the oil is DOTP or closely related isomers. The aqueous layer collected from the bottom of the Dean Stark trap was analyzed using gas chromatography combined with a flame ionization detector (GC/FID) and the presence of ethylene glycol was determined.

Example 2

In order to demonstrate that undissolved reaction products combusted at 800° C. can catalyze the reaction to form di-octyl-terephthalate (DOTP) and ethylene glycol (EG) two experiments were conducted using post-industrial (PI) PET carpet. Undissolved reaction products collected in Example 1 were heated at 800° C. in a muffle furnace for 3 hours. This operation effectively oxidized all polymers present in PI PET to gas leaving behind just a mineral mixture. It is well known that exposure of calcium carbonate mineral to ≥800° C. results in emission of carbon dioxide and conversion to calcium oxide. The mineral mixture was transferred into a large jar and tightly sealed while allowing it to cool.

Example 3

0.276 g of the mineral mixture obtained in Example 2 was added to a 250 ml 2 neck flask containing 16.5 g of PET carpet. This mass ratio resulted in 1.6 wt % of mineral mixture relative to the utilized PET carpet material. The experiment was performed utilizing the experimental apparatus described in Example 1. 39 ml of 2-ethyl-1-hexanol (EH) alcohol was added to the flask, 8.8 ml of 2-ethyl-1-hexanol was added to the Dean Stark trap and 1 ml water was injected into the bottom the Dean Stark trap (DS trap). The mixture was heated to reflux for 4 hours. A syringe was used to withdraw the top layer from the Dean Stark trap and 6.89 g of the liquid was collected (DS trap tops). The 2.24 g from the bottom layer of Dean Stark trap (DS trap bottoms) was then collected.

A distillation head was connected to the flask and liquid was distilled with a heating bath temperature of about 200° C. The flask was allowed to briefly cool and weak vacuum, about ½ atmosphere, was applied. The additional distillate was collected until at an overheads temperature reached 78° C. and a heating bath temperature reached 200° C. Following another period of brief cooling, strong vacuum, initially 50 Pa, was applied and additional distillate was collected to a maximum overheads temperature of 85° C. at 19 Pa and 200° C. bath temperature. The distillation receiver was found to contain 22.1 g of clear liquid (recovered 2-ethyl-1-hexanol). A new distillation receiver was fitted and strong vacuum was applied. Distillate was collected until a maximum overheads temperature of 166° C. and 14.1 Pa pressure with an oil bath at 218-220° C. was reached. Vacuum was broken and heat was removed after the overheads temperature cooled down to 120° C. The receiver contained 13.32 g of slight yellow/amber tinged oil (crude DOTP). Based on the obtained yield of obtained crude DOTP it was determined that 0.807 g crude DOTP per gram PET carpet can be formed using calcined mineral mixture as a catalyst. It was also determined that the color differences in the DOTP oil obtained using calcined mineral mixture as a catalyst and the DOTP oil obtained in the Example 1 using $Ti(OC_3H_7)_4$ as a reaction catalyst were minimal.

The undissolved reaction products cooled down and then an amount was scraped out of the reaction flask. The residue was then cleaned out entirely and the amount of undissolved reaction products was estimated by mass balance to be about 10.15 g.

GC/FID analysis of the crude DOTP isolated from Example 3 indicated very similar levels of purity to those found in example 1: 96.6% DOTP and 2.5% meta isomer (dioctyl isophthalic acid) in Example 3 vs 95.5% of DOTP and 3% of meta isomer in Example 1. High-Performance Liquid Chromatography (HPLC) analysis (with diode array ultraviolet (UV)/visible (VIS) detector) also demonstrated a similar level of purity indicating that there are no major impurities that fail to elute through GC.

Furthermore, GC analysis indicated that recovered 2-ethyl-1-hexanol alcohol collected in this experiment (22.1 g clear liquid) is nearly pure and is substantially free of ethylene glycol. These findings are of particular interest, as they demonstrate that 2-ethyl-1-hexanol alcohol can be reused. As one of ordinary skill in the art would readily appreciate, due to the similarity of the boiling points of 2-ethyl-1-hexanol and ethylene glycol, the formation of uncontaminated 2-ethyl-1-hexanol is unexpected. GC analysis of the DS trap tops (6.89 g) indicated that about 2% of the material is ethylene glycol and the remainder is 2-ethyl-1-hexanol. These results also demonstrate that this 2-ethyl-1-hexanol can be also reusable as DS trap tops without a need in any additional expensive purification steps.

GC analysis indicated that substantially all ethylene glycol is contained in the DS trap bottoms (2.24 g, experiment 1), demonstrating that minimal distillation would be required to isolate pure ethylene glycol. These results also indicate that implementation of the inventive method can result in significant cost reduction in diols' production.

Example 4

A reaction with 18.2 g PET carpet and 540 ppm $Ti(OC_3H_7)_4$ catalyst was performed in the same manner as described in Example 1, producing about 15.32 g crude DOTP having a bright yellow color, indicating that 0.847 g crude DOTP per gram PET carpet is obtained. Comparison of the yield of crude DOTP from Example 3, 0.807 g crude DOTP/g carpet, with amount of the crude DOTP/g carpet obtained in Example 4, 0.847 g crude DOTP/g carpet, clearly indicates high effectiveness of both of the catalysts.

Example 5

In order to demonstrate that calcined mineral mixture (at 800° C.) obtained from combusting the post-consumer carpet comprising PET can be also a suitable catalyst for producing DOTP and EG the following experiment was conducted. Several pieces of post-consumer carpet comprising PET were cut in half and separated into two groups. The first group with a mass of 21.65 g was reacted and isolated as in Example 3 yielding 12.84 g of crude DOTP or 32.9 mmol DOTP. The second group of carpet (with a mass of 21.35 g) was exhaustively digested in aqueous NaOH at reflux, filtered, and the filtrate was acidified and dried yielding 7.74 g of terephthalic acid (TPA) or 46.6 mmol of terephthalic acid (TPA). This number of mmol represents the total number of mmol of PET repeat units present in the carpet mixture. Comparison of the number of mmol of DOTP isolated and the number of mmol of TPA isolated indicates that the yield of the reaction to make DOTP from PCCPET with mineral mixture catalysis is: reaction % yield=100*((32.9 mmol DOTP/21.65)/(46.6 mmol TPA/21.35))=69.6%.

The invention claimed is:

1. A process for producing an ester comprising:
   (a) providing reclaimed carpet material comprising a polyester component comprising a terephthalic unit; and
   (b) reacting the polyester component with an alcohol having from 6 to 20 carbon atoms and under conditions effective to produce a terephthalate ester; wherein the reclaimed carpet material comprises one or more additional components that remain unreacted after reacting the polyester component with the alcohol;
   (c) separating the unreacted components from the produced terephthalate ester; and
   (d) combusting the separated unreacted components to form an ash component.

2. The process of claim 1, wherein the reclaimed carpet material further comprises at least one of a face fiber, a mineral filler, a backing material, an adhesive composition, a contaminant, or any combinations thereof.

3. The process of claim 2, wherein the mineral filler comprises calcium carbonate.

4. The process of claim 2, wherein the backing material comprises a polyolefin, polyurethane, polyester, polyvinyl chloride or any combinations thereof.

5. The process of claim 2, wherein the adhesive composition comprises at least one homogeneously branched ethylene polymer comprising interpolymer of ethylene with at least one $C_3$-$C_{20}$ α-olefin.

6. The process of claim 2, wherein the adhesive composition comprises a crosslinked styrene-butadiene copolymer, a crosslinked ethylene vinyl acetate copolymer, or a combination thereof.

7. The process of claim 1, wherein the polyester component comprises polyethylene terephthalate, polypropylene terephthalate, polybutylene terephthalate, copolymers thereof, or any combinations thereof.

8. The process of claim 1, wherein the polyester component is present in at least one of a carpet face fiber, a backing material, or an adhesive composition.

9. The process of claim 1, wherein the alcohol comprises a straight chain, branched, cyclic aliphatic group, an aromatic group, an alkaryl group or an aralkyl group.

10. The process of claim 1, wherein the alcohol comprises hexanol, 2-ethyl-1-hexanol, isonanol, isodecanol, isoeicosanol, octanol, decanol, tricadenol, pentadecanol, or any combinations thereof.

11. The process of claim 1, wherein the conditions effective to produce the terephthalate ester comprise the presence of a catalyst.

12. The process of claim 11, wherein the catalyst is present in an ash component.

13. The process of claim 12, wherein the ash component contains CaO.

14. The process of claim 11, wherein the catalyst is not acidic.

15. The process of claim 1, wherein the conditions effective to produce the terephthalate ester further comprise a temperature in the range of from about 160° C. to about 260° C.

16. The process of claim 1, wherein the conditions effective to produce the terephthalate ester further comprise a period of about 0.5 hours to about 12 hours.

17. The process of claim 1, wherein the produced ester comprises a terephthalate ester having a general formula (I):

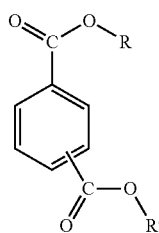

wherein R and R' are the same or different and comprise a straight chain, branched or cyclic aliphatic group, an aromatic group, an alkaryl group or an aralkyl group, each group having from 6 to 20 carbon atoms.

18. The process of claim 17, wherein R and R' are the same or different and comprise a straight chain or a branched alkyl group having from 6 to 20 carbon atoms.

19. The process of claim 17, wherein at least 90% by weight of the produced terephthalate ester is

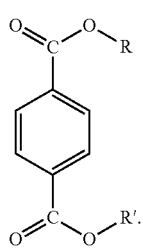

20. The process of claim 17, wherein about 10% or less by weight of the produced ester is:

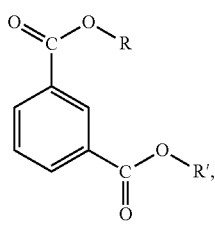

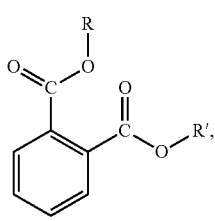

or a combination thereof.

21. The process of claim 17, wherein the terephthalate ester having a general formula (I) comprises di-n-hexyl terephthalate, dioctyl terephthalate, diisononyl terephthalate, diisodecyl terephthalate, di-n-octyl n-decyl terephthalate, di-n-tridecyl n-pentadecyl terephthalate, or diisoeicosyl terephthalate.

22. The process of claim 1, wherein reacting under the conditions effective to produce the terephthalate ester further produces a diol.

23. The process of claim 22, wherein the diol comprises at least one of ethylene glycol, 1,3-propnediol, or 1,4-butanediol.

24. The process of claim 1, wherein the separated unreacted components are combusted at a temperature of at least about 800° C. for at least 0.5-3.0 hours to form an ash component.

25. The process of claim 24, wherein the ash component is suitable for use as a reaction catalyst in a transesterification reaction.

26. A process for recycling a reclaimed carpet material comprising:
reacting a reclaimed carpet material comprising a polyester component comprising a terephthalic unit with an alcohol having from 6 to 20 carbon atoms in the presence of a catalyst at a temperature from about 160° C. to about 260° C. to form a reaction mixture, and wherein the reaction mixture comprises:
(a) a terephthalate ester derived from the reclaimed carpet material;
(b) a diol, wherein substantially all of the diol is derived from the polyester component present in the reclaimed carpet material; and
(c) unreacted products; and
(d) separating the unreacted components from the reaction mixture and combusting the separated unreacted components to form an ash component.

27. The process of claim 26, wherein the polyester component comprises polyethylene terephthalate, polypropylene terephthalate, polybutylene terephthalate, copolymers thereof, or any combinations thereof.

28. The process of claim 26, wherein the polyester component is present in at least one of a carpet face fiber, a backing material, or an adhesive composition.

29. The process of claim 26, wherein the alcohol comprises a straight chain, branched, cyclic aliphatic group, an aromatic group, an alkaryl group or an aralkyl group.

30. The process of claim 26, wherein the alcohol comprises hexanol, 2-ethyl-1-hexanol, isononanol, isodecanol, isoeicosanol, octanol, decanol, tricadenol, pentadecanol, or any combinations thereof.

31. The process of claim 26, further comprising separating the terephthalate ester, and diol from the reaction mixture.

32. The process of claim 31, wherein the separated terephthalate ester comprises a terephthalate ester having a general formula (I):

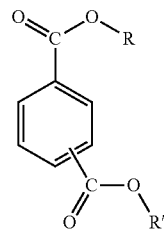

wherein R and R' are the same or different and comprise a straight chain, branched or cyclic aliphatic group, an aromatic group, an alkaryl group or an aralkyl group, each group having from 6 to 20 carbon atoms.

33. The process of claim 32, wherein R and R' are the same or different and comprises a straight chain or a branched alkyl group having from 6 to 20 carbon atoms.

34. The process of claim 32, wherein at least 90% by weight of the separated terephthalate ester is

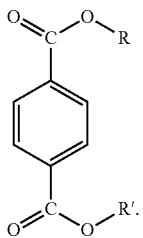

(II)

35. The process of claim 32, wherein about 10% or less by weight of the separated terephthalate ester is:

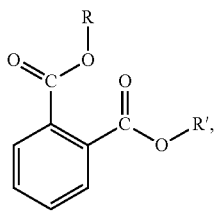

(III)

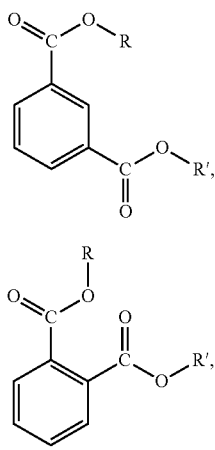

(IV)

or a combination thereof.

36. The process of claim 26, wherein the separated terephthalate ester comprises di-n-hexyl terephthalate, dioctyl terephthalate, diisononyl terephthalate, diisodecyl terephthalate, di-n-octyl n-decyl terephthalate, di-n-tridecyl n-pentadecyl terephthalate, or diisoeicosyl terephthalate.

37. The process of claim 26, wherein the diol comprises at least one of ethylene glycol, 1,3-propanediol, or 1,4-butanediol.

38. A process for producing a diol comprising:
(a) providing reclaimed carpet material comprising a polyester component comprising a terephthalic unit; and
(b) reacting the polyester component with an alcohol having from 6 to 20 carbon atoms under conditions effective to produce a diol, wherein the reclaimed carpet material comprises one or more additional components that remain unreacted after the reaction of the polyester component with the alcohol;
(c) separating unreacted components from the diol; and
(d) combusting the separated unreacted components to form an ash component;
wherein substantially all of the produced diol is derived from the polyester component present in the reclaimed carpet material.

39. The process of claim 38, wherein the polyester component comprises polyethylene terephthalate, polypropylene terephthalate, polybutylene terephthalate, or any combinations thereof.

40. The process of claim 38, wherein the polyester component is present in at least one of a carpet face fiber, a backing material, or an adhesive composition.

41. The process of claim 38, wherein the alcohol comprises a straight chain, branched, cyclic aliphatic group, an aromatic group, an alkaryl group or an aralkyl group.

42. The process of claim 38, wherein the alcohol comprises hexanol, 2-ethyl-1-hexanol, isonanol, isodecanol, isoeicosanol, octanol, decanol, tricadenol, pentadecanol, or any combinations thereof.

43. The process of claim 38, wherein the diol comprises at least one of ethylene glycol, 1,3-propanediol, or 1,4-butanediol.

44. The process of claim 1, wherein about 15-40% of the mass of the terephthalate ester based on a ratio of molecular weights is derived from the polyester component present in the reclaimed carpet material.

45. The process of claim 26, wherein about 15-40% of the mass of the terephthalate ester based on a ratio of molecular weights is derived from the polyester present in the reclaimed carpet material.

46. The process of claim 26, wherein the step of combusting the separated unreacted components is at a temperature of at least about 800° C. for at least 0.5-3.0 hours.

47. The process of claim 38, wherein the step of combusting the separated unreacted components is at a temperature of at least about 800° C. for at least 0.5-3.0 hours.

* * * * *